United States Patent
Breton et al.

(12) 
(10) Patent No.: US 6,241,993 B1
(45) Date of Patent: *Jun. 5, 2001

(54) THERAPEUTIC/COSMETIC COMPOSITIONS COMPRISING BRADYKININ ANTAGONISTS FOR TREATING SENSITIVE HUMAN SKIN

(75) Inventors: Lionel Breton, Versailles; Olivier De Lacharriere, Paris, both of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/087,803

(22) Filed: Jun. 1, 1998

Related U.S. Application Data

(63) Continuation of application No. 08/688,738, filed on Jul. 31, 1996, now Pat. No. 5,849,312.

(30) Foreign Application Priority Data

Jul. 31, 1995 (FR) .................................................. 95 09304

(51) Int. Cl.$^7$ ...................................................... A61K 7/48
(52) U.S. Cl. .............................. 424/401; 424/43; 424/49; 424/70.1; 424/489; 514/844; 514/846; 514/936; 514/944
(58) Field of Search ................................ 424/401, 43, 49, 424/70.1, 489; 514/844, 846, 936, 944

(56) References Cited

U.S. PATENT DOCUMENTS 5,789,383 * 8/1998 Wirth et al. ............................. 514/15
5,849,312 * 12/1998 Breton et al. ......................... 424/401

FOREIGN PATENT DOCUMENTS

| 0552106 | 7/1993 | (EP) . |
| 0661058 | 7/1995 | (EP) . |
| 2271774 | 4/1994 | (GB) . |
| 83/01252 | 4/1983 | (WO) . |
| 93/14084 | 7/1993 | (WO) . |

OTHER PUBLICATIONS

Neuroscience, vol. 48, No. 4, 1992, pp. 963–968.
British Journal of Pharmacology, vol. 110, No. 2, Oct. 1993, pp. 772–76.
British Journal of Pharmacology, vol. 104, No. 3, Nov. 1991, pp. 738–742.
British Journal of Pharmacology, vol. 109, No. 1, 1993, pp. 259–264.
British Journal of Dermatology, vol. 124, No. 4, 191, pp. 324–328.
Contact Dermatitis, vol. 19, No. 5, 1988, pp. 351–354.

* cited by examiner

*Primary Examiner*—Diana Dudash
*Assistant Examiner*—S Sharareh
(74) *Attorney, Agent, or Firm*—Burns, Doane, Swecker & Mathis, L.L.P.

(57) ABSTRACT

Topically applicable pharmaceutical/dermatological/cosmetic compositions well suited for the therapeutic treatment or care of sensitive human skin, hair, mucous membranes, nails and/or the scalp, in particular for reducing or avoiding the skin-irritant side effects of a variety of bioactive agents, for example the α-hydroxy and β-hydroxy acids, comprise a therapeutically/cosmetically effective amount of at least one bradykinin antagonist.

56 Claims, No Drawings

THERAPEUTIC/COSMETIC COMPOSITIONS COMPRISING BRADYKININ ANTAGONISTS FOR TREATING SENSITIVE HUMAN SKIN

This application is a continuation of application Ser. No. 08/688,738, filed Jul. 31, 1996 U.S. Pat. No. 5,849,312.

BACKGROUND OF THE INVENTION

1. Technical Field of the Invention

The present invention relates to the formulation of a bradykinin antagonist into topically applicable cosmetic, pharmaceutical or dermatological compositions, for the treatment of sensitive human skin, as well as to therapeutic/cosmetic compositions containing a bradykinin antagonist for reducing or eliminating completely the irritant effects elicited by certain active agents, and especially by certain bioactive agents conventionally employed in the cosmetics, pharmaceutical and/or dermatological arts.

2. Description of the Prior Art

It is known to this art that certain skins are more sensitive than others. The symptoms of sensitive skin were heretofore poorly characterized and the problem of these skins was, as a result, poorly defined; the exact mechanism involved in the sensitivity—nonallergic cutaneous hyperreactivity—of the skin, was unknown. In certain quarters it was believed that a sensitive skin was a skin which reacted to cosmetic products, while others believed that it concerned a skin which reacted to a variety of external factors, not necessarily associated with cosmetic and/or dermatological products.

Certain tests have been conducted in attempting to define sensitive skin, for example tests using lactic acid and DMSO which are known to be irritant substances: see, for example, the article by K. Lammintausta et al, *Dermatoses*, 36, pages 45–49 (1988); and the article by T. Agner and J. Serup, *Clinical and Experimental Dermatology*, 14, pages 214–217 (1989). However, these tests did not make it possible to characterize sensitive skin completely.

Moreover, sensitive skin was likened to allergic skin.

Taking account of the ignorance of the characteristics of sensitive skin, it was hitherto very difficult to treat it and it was treated indirectly, for example by limiting, in the cosmetic or dermatological compositions, active species eliciting an irritant effect, such as surfactants, preservatives or perfumes, as well as certain otherwise bioactive agents.

The assignee hereof has now conducted many clinical tests and has been able to determine the symptoms associated with sensitive skin. These symptoms are, in particular, subjective signs, which are essentially "dysaesthesic sensations." By the term "dysaesthesic sensations" are intended more or less painful sensations experienced in an area of skin, such as stinging, tingling, itching or pruritus, burning, inflammation, discomfort, pulling, etc.

The assignee hereof has also been able to demonstrate that a sensitive skin is not an allergic skin. Indeed, an allergic skin is a skin which reacts to an external agent, an allergen, which triggers an allergic reaction. This is an immunological response which occurs only when an allergen is present and which affects only sensitized individuals. To the contrary, the essential characteristic of sensitive skin, according to the assignee hereof, is a mechanism of response to external factors, which may be the case for any individual, even if the individuals said to have sensitive skin react faster thereto than the other individuals. This mechanism is not immunological.

It has now been determined that sensitive skin can be divided into two major clinical forms; irritable skin and intolerant skin.

An irritable skin is a skin which reacts by a pruritus, namely, by itching or by stinging, to various factors such as the environment, emotions, foods, the wind, rubbing, shaving, soap, surfactants, hard water having a high calcium concentration, temperature variations, or wool. In general, these signs are associated with a dry skin with or without dartres, or with a skin which displays an erythema.

An intolerant skin is a skin which reacts, by sensations of inflammation or pulling, but also in the same manner as irritable skin by a pruritus, i.e., by itching or stinging. Intolerant skin is also characterized by tingling and/or redness to various factors such as the environment, emotions and foods. In general, these signs are associated with an erythema and with a skin with or without dartres.

In general, sensitive skin is defined by a specific reactivity of the skin. This hyperreactivity may, in particular, be triggered by environmental, emotional or dietary factors or, alternatively, by the application of or contacting with cosmetic or dermatological products. This hyperreactive state which defines sensitive skin distinguishes such skin from the ubiquitous reactivity initiated by irritant agents, which induce a skin irritation in virtually all individuals.

This hyperreactive state is experienced and recognized by individuals suffering therefrom, as a "sensitive skin."

"Sensitive" scalps have a more unequivocal clinical semeiology: the sensations of pruritus and/or of stinging and/or of inflammation are essentially triggered by local factors such as rubbing, soap, surfactants, hard water having a high calcium concentration, shampoos or lotions. These sensations are also sometimes triggered by factors such as the environment, emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions, and in the crook of the elbow) and the feet, sensitive skin is reflected in pruriginous sensations and/or dysaesthesic sensations (inflammation, stinging) associated in particular with sweat, rubbing, wool, surfactants, hard water having a high calcium concentration and/or temperature variations.

The assignee hereof has also developed a test in order to determine whether or not a skin is sensitive. Indeed, after having carried out a multitude of tests for the purpose of defining sensitive skin, it has now surprisingly been found that there is a nexus between individuals with sensitive skin and those who react to a topical application of capsaicin.

The capsaicin test entails applying, to about 4 $cm^2$ of skin, 0.05 ml of a cream containing 0.075% of capsaicin and in noting the appearance of subjective signs induced by this application, such as stinging, burning and itching. In individuals having sensitive skin, these signs appear between 3 and 20 minutes after application and are succeeded by the appearance of an erythema which begins at the edge of the zone of application.

Hitherto, capsaicin was used as a medicinal active agent, in particular for treating zona pains. Capsaicin induces a release of neuropeptides from sensitive nerve fibers, and in particular of tachykinins and of CGRP (peptide derived from the calcitonin gene: Calcitonin Gene Related Peptide) which originate from epidermal and dermal nerve endings. It has been observed that the physiopathological pattern common to all conditions of sensitive skin was associated with a marked ability to release neuropeptides, and more particularly Substance P and CGRP, into the skin. It is known, moreover, that these neuropeptides released by sensitive epidermal nerve endings induce a cascade of biochemical events whose first steps involve mastocytes. The binding of these neuropeptides, and in particular Substance P, to the mastocyte receptors induces a release of a number of proinflammatory mediators.

SUMMARY OF THE INVENTION

It has now been determined that one of the essential characteristics of sensitive skin (reactions of skin irritation and intolerance) are associated, in particular, with the release of these neuropeptides, induced by bradykinin which binds to nerve fibers containing Substance P and CGRP.

Bradykinin is an inflammatory nonapeptide originating in the plasma, which is released from a kininogen precursor by a plasma protease recognized as Kallikrein (EC 3.4.21.24). Bradykinin is involved in a large number of physiopathological disorders, including hypotension, contraction of smooth muscle in the digestive and respiratory tracts and in the uterus, pain, the proliferation of connective tissue and the release of various inflammation mediators, for example cytokines, leukotrienes and prostaglandins.

Bradykinin exerts its activity by binding to two types of receptor, referred to as bradykinin $B_1$ and $B_2$ receptors.

Moreover, the release of bradykinin may initiate, directly and independently of the mechanisms described below, an inflammatory reaction which is indicated by an erythema, an edema and a pruritus.

Thus, it has now been determined that the use of a bradykinin antagonist permits the preventive and/or curative therapeutic treatment of sensitive skin, possibly by inhibiting the release of Substance P and/or of CGRP, which are themselves responsible for the release of various inflammation mediators responsible for the reactivity of sensitive skin.

To treat sensitive skin, bradykinin antagonists are hereby employed. Indeed, it has now surprisingly been found that the formulation of bradykinin antagonists into a cosmetic, pharmaceutical or dermatological composition avoids the irritation and/or dysaesthesic sensations in and/or pruritus of the skin and/or of the mucous membranes.

Briefly, the present invention features the formulation of at least one bradykinin antagonist into topically applicable compositions comprising a cosmetically, pharmaceutically or dermatologically acceptable medium, for treating sensitive skin.

The present invention also features the use of at least one bradykinin antagonist for preventing and/or combating skin irritations and/or dartres and/or erythema and/or inflammation sensations and/or dysaesthesia and/or pruritus of the skin and/or of the mucous membranes.

DETAILED DESCRIPTION OF BEST MODE AND SPECIFIC/PREFERRED EMBODIMENTS OF THE INVENTION

More particularly according to the present invention, by the term "bradykinin antagonist" is intended any substance capable of inhibiting the release and/or synthesis and/or receptor binding of bradykinin. Antagonists which inhibit the receptor binding of bradykinin are agents specific for the bradykinin type 1 ($B_1$) and/or type 2 ($B_2$) receptor.

According to this invention, either a single or several bradykinin antagonist(s) can be used. For example, a release and/or synthesis antagonist in combination with a $B_1$ and/or $B_2$ receptor antagonist can be used.

In addition, the formulation of bradykinin antagonists into topically applicable cosmetic, pharmaceutical or dermatological compositions containing irritant species (α-hydroxy acids, retinoids, benzoyl peroxide, etc.), permits reducing, or even completely eliminating the irritation reactions usually initiated by these compounds. These irritation reactions are indicated, following application, by dysaesthesic sensations (inflammation, burning sensations, itching or pruritus, stinging or pulling sensations, etc.), and/or by redness, and/or by edema. These states of irritation may also be indicated, some time after application, by the persistence, appearance or reappearance of the abovementioned dysaesthesic sensations and/or by redness and/or by squama; these states of skin irritation may be manifested by the appearance of skin xerosis patches and/or dartres.

Thus, the formulation of bradykinin antagonists into cosmetic, pharmaceutical or dermatological irritant compositions makes it possible to reduce, or even eliminate altogether, the irritation reactions usually triggered by certain active species.

Accordingly, this invention also features novel therapeutic/cosmetic compositions containing, in a cosmetically, pharmaceutically or dermatologically acceptable medium, at least one entity eliciting an irritant side effect, and at least one bradykinin antagonist of this effect.

By a "cosmetically, dermatologically or pharmaceutically acceptable medium" is intended a medium which is compatible with the skin, the scalp, the nails and the mucous membranes. The composition containing a bradykinin antagonist may thus be topically applied to the face, the neck, the hair and the nails, or to any other area of body skin such as the major folds (axillary and submammary regions, the crook of the elbow, and the like).

In order for a substance or chemical species to be recognized as a bradykinin receptor antagonist, it must comply, in particular, with the following characteristics:

(a) It must have a selective affinity for the receptors specific for this compound: of type $B_1$ and/or $B_2$.

The experimental models used are prepared by culturing mesenteric aorta cells (receptor binding to $B_1$ receptors according to the technique described by J. P. Galizzi, *Brit. J. Pharmacol.*, 113, 389 (1994)) and/or on intestine (receptor binding to $B_2$ receptors according to the technique described by R. M. Burch, *Biotech. Update* (Dupont-Nen), 7, 2 (1992)).

(b) It must elicit a bradykinin receptor antagonist pharmacological activity, i.e., inducing a coherent pharmacological response in specific tests.

The pharmacological activity is, in this instance, evaluated on organs isolated according to the methodology described by N. E. Rhaleb et al, *Brit. J. Pharmacol.*, 94, 445 (1990) as regards an antagonist activity of $B_1$ and/or $B_2$ type.

For an active species to be recognized as a bradykinin release and/or synthesis antagonist, it must, in particular, possess the following characteristic:

(c) It must inhibit the release of bradykinin.

Preferred bradykinin antagonists are those employed conventionally for the treatment of allergic states, inflammatory states, burns and septic shock.

Exemplary such compounds include Icatibant, HOE140, CP0364, CP0127, NPC-17731 and the compounds indicated in EP-578,521, U.S. Pat. No. 5,212,182, EP-564,972, EP-548,825, JP-93/255107, EP-552,106, FR-2,686,343 and WO-93/11,789.

In the compositions according to the invention, the bradykinin antagonists are preferably employed in an amount ranging from 0.000001% to 5% by weight relative to the total weight of the composition, and in particular in an amount ranging from 0.0001% to 0.1% by weight relative to the total weight of the composition.

The compositions of the invention may be formulated into any pharmaceutical form normally employed for topical application, in particular in the form of aqueous, aqueous/alcoholic or oily solutions or dispersions of the lotion or serum type, anhydrous or lipophilic gels, emulsions of liquid or semi-liquid consistency of the milk type, obtained by dispersion of a fatty phase in an aqueous phase (O/W) or conversely (W/O), or suspensions or emulsions of smooth, semi-solid or solid consistency of the cream or gel type, or alternatively microemulsions, microcapsules or microparticles, or vesicle dispersions of ionic and/or non-ionic type. These compositions are formulated according to the conventional techniques.

They may also be used for the hair or scalp in the form of aqueous, alcoholic or aqueous/alcoholic solutions, or in the form of creams, gels, emulsions or mousses or alternatively in the form of aerosol compositions also containing a propellant under pressure.

The amounts of the various constituents of the compositions according to the invention are those conventionally used in the fields under consideration.

These compositions constitute, in particular, cleansing, protective, treatment or care creams for the face, for the hands, for the feet, for the major anatomical folds or for the body (for example day creams, night creams, makeup-removing creams, foundation creams and antisun creams), fluid foundations, makeup-removing milks, body milks for protection or care, antisun milks or, preferably, after-sun milks, lotions, gels or mousses for skin care, such as cleansing or disinfecting lotions, antisun lotions, artificial tanning lotions, compositions for the bath, deodorizing compositions containing a bactericide, aftershave gels or lotions, hair-removing creams, compositions to counter insect bites, pain-relief compositions or compositions for treating certain skin diseases such as severe pruritus, rosacea, acne, leg ulcers, psoriasis, pustules and vibices.

The compositions according to the invention may also be formulated as solid preparations constituting cleansing bars or soaps.

The bradykinin antagonists may also be incorporated into various haircare or hair treatment compositions, and in particular shampoos, which may be antiparasitic shampoos, hairsetting lotions, treating lotions, styling creams or gels, dye compositions (in particular oxidation dyes) optionally in the form of coloring shampoos, restructuring lotions for the hair, permanent-wave compositions (in particular compositions for the first stage of a permanent-waving operation), lotions or gels for combating hair loss, and the like.

The compositions of the invention may also be formulated for buccodental use, for example as a toothpaste or a mouthwash. In this event, the subject compositions may contain adjuvants and additives which are conventional for compositions for buccal use and, in particular, surfactants, thickeners, wetting agents, polishing agents such as silica, various active ingredients such as fluorides, in particular sodium fluoride, and optionally sweeteners such as sodium saccharinate.

When the compositions of the invention are formulated as an emulsion, the proportion of the fatty phase advantageously ranges from 5% to 80% by weight, and preferably from 5% to 50% by weight, relative to the total weight of the composition. The oils, the emulsifiers and the coemulsifiers used in the compositions in emulsion form are selected from among those used conventionally in the cosmetics, pharmaceutical or dermatological fields. The emulsifier and the coemulsifier are advantageously present in the composition at a proportion ranging from 0.3% to 30% by weight, and preferably from 0.5% to 30% or more preferably from 0.5% to 20% by weight, relative to the total weight of the composition. The emulsion may also contain lipid vesicles.

When the compositions of the invention comprise an oily solution or gel, the fatty phase may constitute more than 90% of the total weight of the composition.

In known manner, the compositions of the invention may also contain additives and adjuvants which are common in the cosmetics, pharmaceutical or dermatological field, such as hydrophilic or lipophilic gelling agents, hydrophilic or lipophilic active agents, preservatives, antioxidants, solvents, fragrances, fillers, screening agents, bactericides, odor absorbers and dyestuffs and colorants. The amounts of these various additives and adjuvants are those used conventionally in the cosmetics, pharmaceutical or is dermatological field and range, for example, from 0.01% to 20% of the total weight of the composition. Depending on their nature, these additives and adjuvants may be introduced into the fatty phase, into the aqueous phase and/or into the lipid spherules.

Exemplary oils which are suitable for the compositions of the invention include mineral oils (liquid petrolatum), plant oils (liquid fraction of karite butter, sunflower oil), animal oils (perhydrosqualene), synthetic oils (Purcellin oil), silicone oils (cyclomethicone) and fluoro oils (perfluoropolyethers). Fatty alcohols, fatty acids (stearic acid) and waxes (paraffin wax, carnauba wax or beeswax) may also be used as fats.

Exemplary emulsifiers according to the invention include glyceryl stearate, polysorbate 60 and the PEG-6/PEG-32/glycol stearate mixture marketed under the trademark Tefose® 63 by Gattefosse.

Exemplary solvents according to the invention include the lower alcohols, in particular ethanol and isopropanol, and propylene glycol.

Exemplary hydrophilic gelling agents which are suitable include carboxyvinyl polymers (carbomer), acrylic copolymers such as acrylate/alkylacrylate copolymers, polyacrylamides, polysaccharides such as hydroxypropyl cellulose, natural gums and clays, and, as lipophilic gelling agents, representative thereof are modified clays such as bentones, fatty acid metal salts such as aluminum stearates, and hydrophobic silica, or else ethyl cellulose and polyethylene.

Exemplary hydrophilic active agents which may be incorporated include proteins or protein hydrolysates, amino acids, polyols, urea, allantoin, sugars and sugar derivatives, water-soluble vitamins, starch and bacterial or plant extracts, in particular those of Aloe vera.

And exemplary lipophilic active agents include retinol (vitamin A) and derivatives thereof, tocopherol (vitamin E) and derivatives thereof, essential fatty acids, ceramides and essential oils.

It is also intended, inter alia, to combine the bradykinin antagonists with bioaffecting active agents useful, in particular, for the prevention and/or treatment of skin conditions, complaints and afflictions. Exemplary of these active agents are:

(1) Agents which modify cutaneous differentiation and/or proliferation and/or pigmentation, such as retinoic acid and isomers thereof, retinol and esters thereof, retinoids, vitamin D and derivatives thereof, estrogens such as estradiol, kojic acid or hydroquinone;

(2) Antibacterial agents, such as clindamycin phosphate, erythromycin or antibiotics from the tetracycline class;

(3) Antiparasitic agents, in particular metronidazole, crotamiton or pyrethroids;

(4) Antifungal agents, in particular compounds belonging to the imidazole class such as econazole, ketoconazole or miconazole or salts thereof, polyene compounds such as amphotericin B, compounds of the allylamine family such as terbinafine, or octopirox;

(5) Steroidal anti-inflammatory agents, such as hydrocortisone, anthralins (dioxyanthranol), anthranoids, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;

(6) Anaesthetics, such as lidocaine hydrochloride and derivatives thereof;

(7) Antipruriginous agents, such as thenaldine, trimeprazine or cyproheptadine;

(8) Antiviral agents, such as acyclovir;

(9) Keratolytic agents, such as alpha- and beta-hydroxycarboxylic acids or beta-ketocarboxylic acids, the salts, amides or esters thereof and more particularly alpha-hydroxy acids such as glycolic acid, lactic acid, malic acid, tartaric acid, citric acid and fruit acids in general, and beta-hydroxy acids such as salicylic acid and derivatives thereof, in particular alkyl derivatives such as 5-n-octanoylsalicylic acid;

(10) Anti-free-radical agents, such as alpha-tocopherol or esters thereof, superoxide dismutases, certain metal chelating agents or ascorbic acid and esters thereof;

(11) Antiseborrhoeic agents, such as progesterone;

(12) Antidandruff agents, such as octopirox or zinc pyrithione;

(13) Anti-acne agents such as retinoic acid or benzoyl peroxide;

(14) Antimetabolites;

(15) Agents for combating hair loss, such as minoxidil;

(16) Antiseptics.

Advantageously, the bradykinin antagonists are combined with compounds or species normally eliciting an irritant side effect, and, especially, active agents used conventionally in the cosmetics, pharmaceutical or dermatological arts. Including a bradykinin antagonist in a cosmetic, pharmaceutical or dermatological composition containing a compound or active agent exhibiting an irritant effect makes it possible to attenuate this irritant effect greatly, or even to eliminate it completely.

In particular, the bradykinin antagonists permit, especially, increasing the amount of cosmetic, pharmaceutical or dermatological active agent relative to the amount normally used, for the purpose of enhancing efficacy.

The irritants according to the invention include, in particular, fragrances, surfactants (ionic or nonionic surfactants), preservatives, certain sunscreens, organic solvents, alcoholic solutions and certain cosmetic, pharmaceutical or dermatological active agents.

In particular, the active agents exhibiting an irritant side effect are selected from among α-hydroxy acids (glycolic acid, lactic acid, malic acid, citric acid, tartaric acid and mandelic acid), β-hydroxy acids (salicylic acid and derivatives thereof), α-keto acids, β-keto acids, retinoids (retinol and esters thereof, retinal, retinoic acid and derivatives thereof, and retinoids, in particular those described in FR-A-2,570,377, EP-A-199,636, EP-A-325,540 and EP-A-402,072), anthralins (dioxyanthranol), anthranoids, peroxides (in particular benzoyl peroxide), minoxidil, lithium salts, antimetabolites, vitamin D and derivatives thereof, hair dyes or colorants (para-phenylenediamine and derivatives thereof, and aminophenols), perfumed alcoholic solutions (fragrances, eau de toilette, aftershave and deodorants), antiperspirants (certain aluminum salts), depilatory or permanent-waving active agents (thiols), depigmenting agents (hydroquinone) and anti-lice active agents (pyrethrin).

Including a bradykinin antagonist in the subject compositions permits, in particular, amplifying the amount of product, and more especially of active agent exhibiting an irritant side effect, by 2 to 10 times compared with the state of the prior art, without experiencing the aforesaid discomforts. Thus, it is possible to formulate the hydroxy acids at up to 50% of the weight of the composition, or the retinoids at up to 5%, without any discomfort.

In particular, the composition comprises a bradykinin antagonist selected from among organic or inorganic species, or one which is contained in extracts recovered from plant or animal cells or from microorganisms.

The present invention also features a cosmetic and/or dermatological treatment or regimen, especially for treating sensitive skin, comprising topically applying a composition as described above, containing at least one bradykinin antagonist in a cosmetically and/or dermatologically acceptable medium, (vehicle, diluent or carrier), to the skin, to the scalp and/or to the mucous membranes.

The cosmetic and/or dermatological treatment process of the invention may be implemented by topically applying the hygiene or cosmetic and/or dermatological compositions as described above, via the usual techniques for applying these compositions. For example: application of creams, gels, salves, sera, lotions, ointments, makeup-removing milks or aftersun compositions to the skin or to dry hair, application of a hair lotion to wet hair, application of shampoos, or application of toothpaste to the gums.

In order to further illustrate the present invention and the advantages thereof, the following specific examples are given, it being understood that same are intended only as illustrative and in nowise limitative.

In said examples to follow, all parts and percentages are given by weight.

EXAMPLE 1

| Lotion for removing makeup from sensitive facial skin: | |
|---|---|
| Icatibant | 0.005 |
| Antioxidant | 0.05 |

-continued

| Lotion for removing makeup from sensitive facial skin: | |
|---|---|
| Isopropanol | 40.00 |
| Preservative | 0.30 |
| Water | qs 100% |

EXAMPLE 2

| Lotion for removing makeup from sensitive facial skin: | |
|---|---|
| CP0127 | 0.001 |
| Antioxidant | 0.05 |
| Isopropanol | 40.00 |
| Preservative | 0.30 |
| Water | qs 100% |

EXAMPLE 3

| Gel for the care of sensitive facial skin: | |
|---|---|
| Icatibant | 0.04 |
| Hydroxypropylcellulose (Klucel H marketed by Hercules) | 1.00 |
| Antioxidant | 0.05 |
| Isopropanol | 40.00 |
| Preservative | 0.30 |
| Water | qs 100% |

EXAMPLE 4

| Care cream for sensitive facial skin (oil-in-water emulsion): | |
|---|---|
| CP0364 | 0.02 |
| Glyceryl stearate | 2.00 |
| Polysorbate 60 (Tween 60 marketed by ICI) | 1.00 |
| Stearic acid | 1.40 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.5 |
| Preservative | 0.30 |
| Water | qs 100% |

EXAMPLE 5

| Anti-wrinkle care cream for sensitive facial skin (oil in-water emulsion): | |
|---|---|
| CP0364 | 0.15 |
| Glyceryl stearate | 2.00 |
| Polysorbate 60 (Tween 60 marketed by ICI) | 1.00 |
| Stearic acid | 1.40 |
| n-Octanoyl-5-salicylic acid | 0.50 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.50 |

-continued

| Anti-wrinkle care cream for sensitive facial skin (oil in-water emulsion): | |
|---|---|
| Preservative | 0.30 |
| Water | qs 100% |

EXAMPLE 6

| Emulsified care gel for treating insect bites (oil-in water emulsion): | |
|---|---|
| Icatibant | 3.00 |
| Purcellin oil (marketed by Dragocco) | 7.00 |
| PEG-6/PEG-32/glycol stearate (Tefose ® 63 marketed by Gattefosse) | 0.30 |
| Preservative | 0.30 |
| Fragrance | 0.40 |
| Carbomer | 0.60 |
| Crotamiton | 5.00 |
| Glycyrrhetinic acid | 2.00 |
| Ethyl alcohol | 5.00 |
| Triethanolamine | 0.20 |
| Water | qs 100% |

EXAMPLE 7

| Pain-relief gel: | |
|---|---|
| CP0364 | 0.03 |
| Hydroxypropylcellulose (Klucel H marketed by Hercules) | 1.00 |
| Antioxidant | 0.05 |
| Lidocaine hydrochloride | 2.00 |
| Isopropanol | 40.00 |
| Preservative | 0.30 |
| Water | qs 100% |

EXAMPLE 8

| Care cream for treating solar erythema on sensitive skin (oil-in-water emulsion): | |
|---|---|
| CP0127 | 0.25 |
| Glyceryl stearate | 2.00 |
| Polysorbate 60 (Tween 60 marketed by ICI) | 1.00 |
| Stearic acid | 1.40 |
| Glycyrrhetinic acid | 2.00 |
| Triethanolamine | 0.70 |
| Carbomer | 0.40 |
| Liquid fraction of karite butter | 12.00 |
| Sunflower oil | 10.00 |
| Antioxidant | 0.05 |
| Fragrance | 0.5 |
| Preservative | 0.30 |
| Water | qs 100% |

EXAMPLE 9

Anti-Winkle Care Cream for Sensitive Facial Skin (Oil-In-Water Emulsion)

The formulation of this example was the same as that of Example 5, except that the n-octanoyl-5-salicylic acid was replaced by a fruit acid mixture (lactic, glycolic, tartaric, citric and malic acids).

EXAMPLE 10

| Gel for treating acne: | |
|---|---|
| All-trans-retinoic acid | 0.05 |
| Icatibant | 0.55 |
| Hydroxypropylcellulose | 1.00 |
| (Klucel H marketed by Hercules) | |
| Antioxidant | 0.05 |
| Isopropanol | 40.00 |
| Preservative | 0.3 |
| Water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable composition which comprises (i) at least one normally skin irritating agent which is contained in an amount which normally elicits skin irritation upon topical application to sensitive skin, wherein said agent is selected from the group consisting of an anti-bacterial agent, an antiparasitic agent, an antifungal agent, an anti-inflammatory agent, an anti-pruriginous agent, an anaesthetic, a keratolytic agent, an anti-free-radical agent, an antiseborrhoeic agent, an antidandruff agent, an antiacne agent, an agent which modifies at least one of differentiation, proliferation and pigmentation of human skin; and (ii) an amount of at least one bradykinin antagonist which is effective to inhibit such irritation when said composition is topically applied to sensitive skin; and (iii) a cosmetically acceptable vehicle, diluent or carrier.

2. A topically applicable cosmetic composition which comprises (i) at least one normally skin irritating agent which is contained in an amount that normally elicits skin irritation upon topical application to sensitive skin, wherein said agent is selected from the group consisting of a fragrance, a surfactant, a preservative, a sunscreen, an organic solvent, an alcohol, and a cosmetic; (ii) an amount of at least one bradykinin antagonist which is effective to inhibit such irritation when such composition is topically applied to sensitive skin; and (iii) a cosmetically acceptable vehicle, diluent or carrier.

3. A topically applicable cosmetic composition which comprises (i) at least one normally skin irritating agent contained in an amount which normally elicits skin irritation upon topical application to sensitive skin, wherein said agent is selected from the group consisting of a hydrophilic gelling agent, a lipophilic gelling agent, a hydrophilic bioactive agent, a lipophilic bioactive agent, a preservative, an antioxidant, a solvent, a fragrance, a filler, a sunscreen, a bactericide, an odor absorber, and a colorant, said hydrophilic bioactive agent being a protein, protein hydrolysate, amino acid polyol, urea, allantoin, sugar, sugar derivative, water-soluble vitamin, starch, bacterial extract, or plant extract, and said lipophilic bioactive agent being retinol, a vitamin A derivative, tocopherol, a vitamin E derivative, an essential fatty acid, a ceramide or an essential oil; (ii) an amount of at least one bradykinin antagonist which is effective to inhibit such irritation when such composition is topically applied to sensitive skin; and (iii) a cosmetically acceptable vehicle, diluent, or carrier.

4. A topically applicable cosmetic composition which comprises (i) at least one normally skin irritating agent contained in an amount which normally elicits skin irritation upon topical application to sensitive skin, wherein said agent is selected from the group consisting of an α-hydroxy acid, a β-hydroxy acid, an α-keto acid, a β-keto acid, a retinoid, an anthralin, an anthranoid, a peroxide, minoxidil, a lithium salt, an antimetabolite, vitamin D, a vitamin D derivative, a hair dye, a hair colorant, an alcoholic perfume, an antiperspirant, a depilatory, a permanent-waving active agent, a depigmenting active agent, and an anti-lice active agent; (ii) an amount of at least one bradykinin antagonist which is effective to inhibit such irritation when such composition is topically applied to sensitive skin; and (iii) a cosmetically acceptable vehicle, diluent, or carrier.

5. The cosmetic composition according to claim 4, wherein said normally skin-irritating bioactive agent is an α-hydroxy acid, or β-hydroxy acid.

6. The cosmetic composition according to claim 1, which is in the form selected from the group consisting of a solution, emulsion, milk, lotion, microemulsion, gel, serum, cream, mousse, soap, shampoo, aerosol, dispersion, toothpaste, mouthwash, microcapsules, and microparticles.

7. The cosmetic composition according to claim 2, which is in the form selected from the group consisting of a solution, emulsion, milk, lotion, microemulsion, gel, serum, cream, mousse, soap, shampoo, aerosol, dispersion, toothpaste, mouthwash, microcapsules, and microparticles.

8. The cosmetic composition according to claim 3, which is in the form selected from the group consisting of a solution, emulsion, milk, lotion, microemulsion, gel, serum, cream, mousse, soap, shampoo, aerosol, dispersion, toothpaste, mouthwash, microcapsules, and microparticles.

9. The cosmetic composition according to claim 4, which is in the form selected from the group consisting of a solution, emulsion, milk, lotion, microemulsion, gel, serum, cream, mousse, soap, shampoo, aerosol, dispersion, toothpaste, mouthwash, microcapsules, and microparticles.

10. The cosmetic composition according to claim 1, wherein the amount of said at least one bradykinin antagonist ranges from 0.0001% to 0.1% by weight thereof.

11. The cosmetic composition according to claim 2, wherein the amount of said at least one bradykinin antagonist ranges from 0.0001% to 0.1% by weight thereof.

12. The cosmetic composition according to claim 3, wherein the amount of said at least one bradykinin antagonist ranges from 0.0001% to 0.1% by weight thereof.

13. The cosmetic composition according to claim 4, wherein the amount of said at least one bradykinin antagonist ranges from 0.0001% to 0.1% by weight thereof.

14. The cosmetic composition according to claim 1, wherein the amount of said at least one bradykinin antagonist ranges from 0.000001% to 5% by weight thereof.

15. The cosmetic composition according to claim 2, wherein the amount of said at least one bradykinin antagonist ranges from 0.000001% to 5% by weight thereof.

16. The cosmetic composition according to claim 3, wherein the amount of said at least one bradykinin antagonist ranges from 0.000001% to 5% by weight thereof.

17. The cosmetic composition according to claim 4, wherein the amount of said at least one bradykinin antagonist ranges from 0.000001% to 5% by weight thereof.

18. A method for treating or preventing adverse skin reactions associated with sensitive skin comprising topically applying to a person with sensitive skin in need of such treatment for such period of time as is required to elicit the desired biological response, an effective amount of at least one bradykinin antagonist sufficient to prevent or treat adverse reactions associated with sensitive skin.

19. A method for preventing or treating adverse skin reactions associated with sensitive skin normally elicited upon topical application of at least one normally skin-irritating agent which method comprises topically administering to a person with sensitive skin in need of such treatment a composition comprising said at least one normally skin-irritating agent in an amount which normally elicits skin irritation upon topical application to sensitive skin and an amount of at least one bradykinin antagonist sufficient to prevent or treat adverse reactions associated with sensitive skin when such composition is topically applied to sensitive skin.

20. The method according to claim 19, wherein said at least one normally skin-irritating agent is selected from the group consisting of an anti-bacterial agent, an antiparasitic agent, an antifungal agent, an anti-inflammatory agent, an anti-pruriginous agent, an anaesthetic, an antiviral agent, a keratolytic agent, an anti-free-radical agent, an antiseborrhoeic agent, an antidandruff agent, an antiacne agent and an agent which modifies at least one of differentiation, proliferation and pigmentation of human skin.

21. The method according to claim 19, wherein said at least one normally skin-irritating agent is selected from the group consisting of a hydrophilic gelling agent, a lipophilic gelling agent, a hydrophilic bioactive agent, a lipophilic bioactive agent, a preservative, an anti-oxidant, a solvent, a fragrance, a filler, a sunscreen, a bactericide, an odor absorber and a colorant.

22. The method according to claim 19, wherein said at least one normally skin-irritating agent is selected from the group consisting of a fragrance, a surfactant, a preservative, a sunscreen, an organic solvent, an alcohol, a cosmetic and a therapeutic agent.

23. The method according to claim 19, wherein said at least one normally skin-irritating agent is selected from the group consisting of an α-hydroxy acid, a β-hydroxy acid, an α-keto acid, a β-keto acid, a retinoid, an anthralin, an anthranoid, a peroxide, minoxidil, a lithium salt, an antimetabolite, vitamin D, a vitamin D derivative, a hair dye, a hair colorant, an alcoholic perfume, an antiperspirant, a depilatory, a permanent-waving active agent, a depigmenting active agent, and an anti-lice active agent.

24. The method according to claim 19, wherein said at least one normally skin-irritating agent is an α-hydroxy acid or β-hydroxy acid.

25. The method according to claim 18, wherein said composition is topically applied to at least one of human hair, skin, nails, scalp and mucous membranes.

26. The method according to claim 19, wherein said composition is topically applied to at least one of human hair, skin, scalp, nails and mucous membranes.

27. The method according to claim 18, wherein such treatment or prevention of sensitive skin results in the treatment or prevention of a side effect selected from the group consisting of skin irritations, dartres, erythema, dysaesthetic sensations, inflammatory sensations, and pruritus of at least one of human skin, hair, nails, and mucous membranes.

28. The method according to claim 19, wherein such treatment or prevention of sensitive skin results in the treatment or prevention of a side effect selected from the group consisting of skin irritations, dartres, erythema, dysaesthetic sensations, inflammatory sensations, and pruritus of at least one of human skin, hair, nails, and mucous membranes.

29. The cosmetic composition of claim 1, wherein the bradykinin antagonist is selected from the groups consisting of: a bradykinin $B_1$ antagonist and a bradykinin $B_1$ and $B_2$ antagonist.

30. The cosmetic composition of claim 29, wherein the amount of said ad least one bradykinin antagonist ranges from 0.0001% to 0.1% by weight thereof.

31. The cosmetic composition of claim 29, wherein the amount of said ad least one bradykinin antagonist ranges from 0.000001% to 5% by weight thereof.

32. The cosmetic composition of claim 1, wherein the bradykinin antagonist is selected from the groups consisting of: Icatibant, CP0364, CP0127 and NPC-17731.

33. The cosmetic composition of claim 32, wherein the amount of said ad least one bradykinin antagonist ranges from 0.0001% to 0.1% by weight thereof.

34. The cosmetic composition of claim 32, wherein the amount of said ad least one bradykinin antagonist ranges from 0.000001% to 5% by weight thereof.

35. The cosmetic composition of claim 2, wherein the bradykinin antagonist is selected from the groups consisting of: a bradykinin $B_1$ antagonist and a bradykinin $B_1$ and $B_2$ antagonist.

36. The cosmetic composition of claim 35, wherein the amount of said ad least one bradykinin antagonist ranges from 0.0001% to 0.1% by weight thereof.

37. The cosmetic composition of claim 35, wherein the amount of said ad least one bradykinin antagonist ranges from 0.000001% to 5% by weight thereof.

38. The cosmetic composition of claim 2, wherein the bradykinin antagonist is selected from the groups consisting of Icatibant, CP0364, CP0127 and NPC-17731.

39. The cosmetic composition of claim 38, wherein the amount of said ad least one bradykinin antagonist ranges from 0.0001% to 0.1% by weight thereof.

40. The cosmetic composition of claim 38, wherein the amount of said ad least one bradykinin antagonist ranges from 0.000001% to 5% by weight thereof.

41. The cosmetic composition of claim 3, wherein the bradykinin antagonist is selected from the groups consisting of: a bradykinin $B_1$ antagonist and a bradykinin $B_1$ and $B_2$ antagonist.

42. The cosmetic composition of claim 41, wherein the amount of said ad least one bradykinin antagonist ranges from 0.0001% to 0.1% by weight thereof.

43. The cosmetic composition of claim 42, wherein the amount of said ad least one bradykinin antagonist ranges from 0.000001% to 5% by weight thereof.

44. The cosmetic composition of claim 3, wherein the bradykinin antagonist is selected from the groups consisting of: Icatibant, CP0364, CP0127 and NPC-17731.

45. The cosmetic composition of claim 44, wherein the amount of said ad least one bradykinin antagonist ranges from 0.0001% to 0.1% by weight thereof.

46. The cosmetic composition of claim 44, wherein the amount of said ad least one bradykinin antagonist ranges from 0.000001% to 5% by weight thereof.

47. The cosmetic composition of claim 41, wherein the bradykinin antagonist is selected from the groups consisting of: a bradykinin $B_1$ antagonist and a bradykinin $B_1$ and $B_2$ antagonist.

48. The cosmetic composition of claim 47, wherein the amount of said ad least one bradykinin antagonist ranges from 0.0001% to 0.1% by weight thereof.

49. The cosmetic composition of claim 47, wherein the amount of said ad least one bradykinin antagonist ranges from 0.000001% to 5% by weight thereof.

50. The cosmetic composition of claim 41, wherein the bradykinin antagonist is selected from the groups consisting of: Icatibant, CP0364, CP0127 and NPC-17731.

51. The cosmetic composition of claim 50, wherein the amount of said ad least one bradykinin antagonist ranges from 0.0001% to 0.1% by weight thereof.

52. The cosmetic composition of claim 50, wherein the amount of said ad least one bradykinin antagonist ranges from 0.000001% to 5% by weight thereof.

53. The method of claim 18, wherein the bradykinin antagonist is selected from the groups consisting of: a bradykinin $B_1$ antagonist and a bradykinin $B_1$ and $B_2$ antagonist.

54. The method of claim 18, the bradykinin antagonist is selected from the groups consisting of: Icatibant, CP0364, CP0127 and NPC-17731.

55. The method of claim 19, wherein the bradykinin antagonist is selected from the groups consisting of: a bradykinin $B_1$ antagonist and a bradykinin $B_1$ and $B_2$ antagonist.

56. The method of claim 19, wherein the bradykinin antagonist is selected from the groups consisting of: Icatibant, CP0364, CP0127 and NPC-17731.

* * * * *